United States Patent [19]

Bommarito

[11] Patent Number: 4,494,837
[45] Date of Patent: Jan. 22, 1985

[54] PUPIL LOCATION GAUGE

[76] Inventor: Paul F. Bommarito, 10684 Martinwood Way, Cupertino, Calif. 95014

[21] Appl. No.: 488,085

[22] Filed: Apr. 25, 1983

Related U.S. Application Data

[63] Continuation-in-part of Ser. No. 179,807, Aug. 20, 1980, Pat. No. 4,381,143, which is a continuation-in-part of Ser. No. 6,340, Jan. 25, 1979, abandoned.

[51] Int. Cl.$^3$ .......................... A61B 3/10; A61B 3/04
[52] U.S. Cl. ..................................... 351/204; 351/230
[58] Field of Search ................... 351/204, 230; 33/200

[56] References Cited

U.S. PATENT DOCUMENTS 1,505,447  8/1924  Uhlemann .......................... 33/200
4,381,143  4/1983  Bommarito ....................... 351/230

Primary Examiner—Rodney B. Bovernick
Attorney, Agent, or Firm—Thomas Schneck

[57] ABSTRACT

A pupil location gauge having an index member movable in relation to a graduated scale may be used in an ophthalmic test lens holder for subjective measurement of both vertical and horizontal pupillary distance. Either monocular or binocular measurements of the pupil location may be made with respect to a spectacle frame.

11 Claims, 9 Drawing Figures

PUPIL LOCATION GAUGE

CROSS REFERENCE TO RELATED APPLICATIONS

This is a continuation-in-part of application Ser. No. 179,807, filed Aug. 20, 1980, now U.S. Pat. No. 4,381,143 which in turn is a continuation-in-part of application Ser. No. 6,340, filed Jan. 25, 1979, now abandoned.

TECHNICAL FIELD

The invention relates generally to ophthalmic instruments and more particularly to a gauge to be used by ophthalmic practitioners in locating the center of a patient's pupil horizontally and vertically with respect to a spectacle frame.

BACKGROUND ART

In prescribing certain ophthalmic lenses, for example progressive power lenses, it is essential for the ophthalmic practitioner to locate the position of a patient's pupil with respect to a spectacle frame which will subsequently hold the lens.

Progressive power lenses have at least two corrective powers and a blend zone between the two power zones. Such lenses are described in the following U.S. Pat. Nos. 3,687,528; 3,785,724; 3,910,691; 3,950,082; 4,002,439; 4,055,379; 4,056,311 and 4,062,629. It is desirable to locate the pupil behind one of the power zones and not in front of or near one of the blend zones. For this reason, laboratories which manufacture ophthalmic lenses ask the practitioner for pupil location relative to the bottom of a frame for which the progressive power lens is to be mounted. Presently, one method of locating the pupil is to take a spectacle frame and apply a piece of masking tape vertically over the front of the frame. The bottom of the frame is marked with a pencil and then the ophthalmic practitioner asks a patient to look at a distant object at eye level. When the patient does this, the ophthalmic practitioner makes another pencil mark on the masking tape at the elevation of the pupil. The practitioner then measures the distance between the two marks on the tape and submits this to the laboratory. One of the problems which is encountered is that the patient is made uncomfortable by the procedure. Moreover, since the tape is a stretchable and sticky material, inaccuracies result, as when the tape sticks to itself in an inchworm fashion. To avoid the inchworming effect, the tape may be stretched, but this causes inaccuracies in the opposite direction.

Horizontal pupillary distance, the distance between the line of sight of one eye and the line of sight of the other eye at a point in a near or far plane, may be measured by another technique. In one method, a narrow red strip is attached to each lens by means of a horizontal elastic member. For measurement of the near pupillary distance, the patient holds a red card with a green square. The red strip is moved across the lens until the patient sees the green square blocked with one eye open. The same is done with the other eye. The distance between the two strips is then measured by a ruler and is the measurement of the horizontal pupillary distance. This technique measures only the near interpupillary horizontal distance, not far, and has not been used to measure the pupil location vertically.

In U.S. Pat. No. 4,381,143, Bommarito discloses an ophthalmic test lens holder for use with spectacle frames by means of which test lenses may be inserted in the plane of said spectacles for measuring and testing purposes. A pair of elongated clamping members having at least one test lens holding bracket attached to one of the members are clamped over a pair of spectacle frames so that a test lens held by the bracket is positioned before a lens socket. Rulings on the clamping member are used to indicate distance and angles for the purpose of adjusting lenses with respect to a frame, for example the height of a bifocal line relative to the frame socket.

It is the object of the invention to devise a gauge for use with an ophthalmic test lens holder similar to the above type by means of which the measurement of the proper pupil position in relation to each power zone of a progressive lens is subjectively measured by the patient rather than objectively by the practitioner locating the pupil elevation while the patient looks at a distant or near object.

It is another object of the invention to devise a gauge which may be used with an ophthalmic lens holder, for measuring both horizontal pupillary distance and vertical pupil location to determine the visual axis.

DISCLOSURE OF INVENTION

The above objects have been met with a pupil location gauge which features a vision interference index member moveably mounted in relation to a graduated scale on a supporting disc. The index member may be moved in relation to the scale by means sensitive to fine adjustment in calibrated relationship to a spectacle frame using a test lens holder which spans the dimension of a spectacle frame socket. In particular, the sensitive moving means may be a fine toothed rack and pinion gear or a fine thread screw. The gauge is mounted in the bracket of the lens holder along with a test lens having the necessary visual correction. The lens holder is clipped over the empty socket of a spectacle frame with the bottom edge of the gauge at a calibrated distance from the bottom of the spectacle lens socket and so that the gauge is positioned in front of the eye pupil. For vertical pupillary distance measurement, the disc bearing the index member is aligned so that the index member is moved vertically. The index member is then moved up and down in fine increments until a point is reached where the patient's view of a distant or near object is blocked by the index member. Because the bottom of the gauge is aligned in a calibrated position with the bottom of the spectacle lens socket, the correct location of the pupil in relation to the spectacle lens for both distant and near viewing may be obtained. Since the patient subjectively determines at what point the distant or near object is blocked, and that position is located accurately by the position of the index member on the integrated graduated scale, there is less chance for inaccuracy than in a separate measurement of the distance by the practitioner with a ruler. The bracket holding the pupil location gauge is not moved, hence there is less chance of disturbing the position of the corrective lens during measurement.

The pupil location gauge is also used to measure the interpupillary distance by means of a modification of the ophthalmic test lens holder of U.S. Pat. No. 4,381,143. To the base portion of a front clamping member of the ophthalmic test lens holder of U.S. Pat. No. 4,381,143, is attached a handle having a horizontal slot having a retainer for holding a graduated rod. A lens holder is attached to each end of the rod by means of the slot. Each holder is then clamped to the center of a socket of the spectacle frame adjusting the distance between the two holders on the graduated rod as necessary. A pupil location gauge is inserted in each holder and then rotated so that the index member is aligned to be moved horizontally with a centering mark on the gauge lined up with a reference mark on the handle. The index member of the pupil location gauge is then moved horizontally by means of the rack and pinion gear until a view of a near or distant object is blocked out by the index member and the amount of correction is added to or subtracted from the distance between the two lens holders as shown on the connecting graduated rod. The measurement is done with one eye open. When both eyes have been measured the view of the object will be blocked out by the index members with both eyes open. The distance between the two handles on the rod plus or minus the correction shown on the pupil location gauge is the horizontal pupillary distance between the two eyes.

An advantage of the invention is that the position of the patient's pupil may be located both vertically and horizontally very accurately with respect to a spectacle frame with or without the patient's normal lens in place.

Another advantage of the invention is that the measurement is a subjective measurement.

BEST MODE FOR CARRYING OUT THE INVENTION

Figure 1:
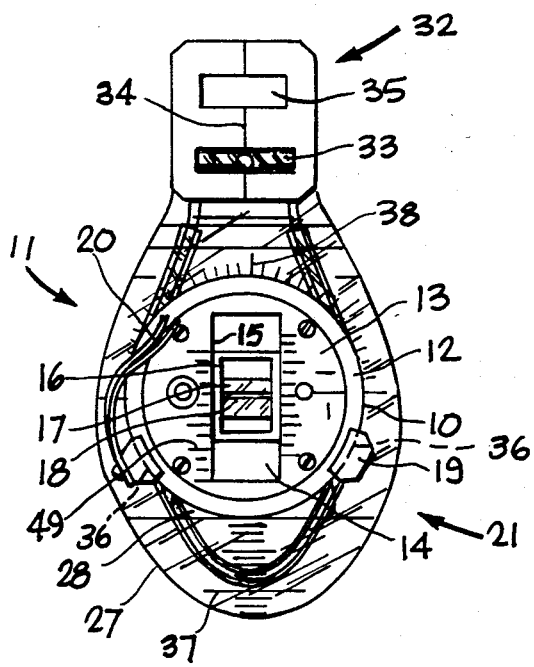
FIG. 1 is a front view showing the pupil location gauge of the present invention in position in an ophthalmic test lens holder.

In FIG. 1, the pupil location gauge 10 is shown in place in an ophthalmic lens holder 11 of the type disclosed in U.S. Pat. No. 4,381,143. The pupil location gauge consists of a disc 12 of standard lens dimension sandwiched to a slightly smaller diameter disc 13. The two discs have a central rectangular aperture 14 and slots between the two discs along the longer lateral walls of the aperture 15 in which a frame insert 16 is slidingly mounted. The edges of the disc along the longer lateral walls of the aperture bear calibrated rulings 49 proximate to the frame insert. The rulings are calibrated with reference to the bottom edge of the gauge and may be correlated with lateral rulings 37 on the lens holder. To the midpoint of the frame is attached a vision interference index member. In the preferred embodiment as shown in FIG. 1, the index member is a transparent filter 17, preferably red, approximately 5 mm by 10 mm, bearing a non-transmissive center line 18, perpendicular to the grooves in the side walls of the aperture. However, any vision interference index means which partially lessens the field of vision so that the image of a near or far object is diminished, is suitable. The pupil location gauge may be mounted in the brackets 19 on the front of the lens holder as shown in FIG. 1, held in place by metal spring 20 or inserted in the rear of the front clamping member 21 through the viewing aperture 28 which is sized to hold the smaller diameter disc 13.

Figure 8:
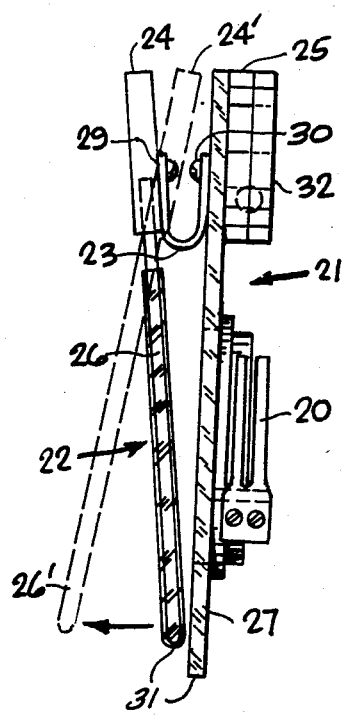
FIG. 8 is a side view of a test lens holder.

As shown in FIGS. 1 and 8, the ophthalmic lens holder 11 used to hold the pupil location gauge consists of a first clamping member 21 connected to a second clamping member 22 by a U-shaped compression spring 23. Clamping members 21 and 22 include a base portion 24 and 25 to which is attached an elongated loop of wire 26 and an elongated piece of flat, transparent plastic material 27 which has a general overall shape similar to the loop and having a viewing aperture 28 in the center thereof which is a round hole slightly smaller than a test lens. Clamping member 27 has a length which is greater than the distance across any socket of a spectacle frame.

U-shaped compression spring 23 is connected to base portion 24 by a fastener assembly 29 and is connected to base portion 25 by a fastener assembly 30. The compression spring 23 serves to bias the ends 31 of the clamping members together, as shown in solid lines in FIG. 8. When base portions 24 and 25 are pressed together usually between the thumb and forefinger of the practitioner's hand, so as to be positioned at 24' and 25, the ends 31 of the clamping members will spread apart as shown at 26' and 27'. When pressure is removed from the base portions, spring 23 will return the clamping members to their original, closed positions.

As shown in FIG. 1, attached to the base portion 25 of member 21 is a handle 32. Handle 32 contains a level 33 and a centrally placed index line 34 for reading graduations on a scaled rod (not shown) through a viewing window 35. The scaled rod, for measuring horizontal distances, is moveably mounted in a horizontal slot in the vernier clip member so that graduation rulings on the rod are viewed through the window 35. Tension to hold the rod in the slot is provided by a metal spring inside the slot.

Figure 9:
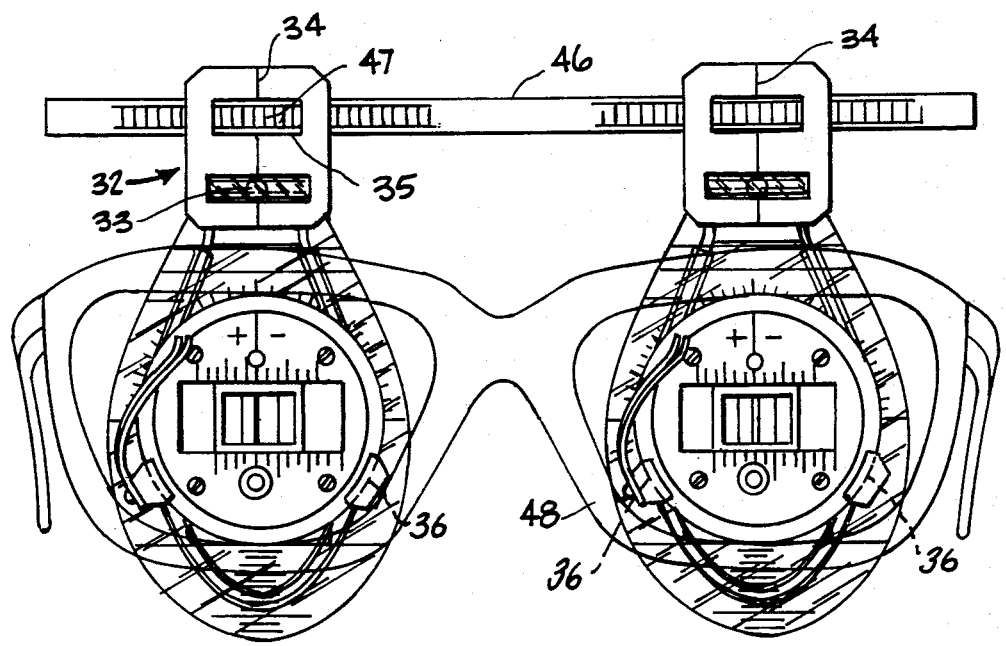
FIG. 9 is a front view of a binocular measurement using two pupil location gauges.

As shown in FIGS. 1 and 9 the test lens support has two brackets 19 provided with a number of grooves 36 having semi circular shape into which the test lens or widest diameter disc of the pupil location gauge seats. The grooves lie in a semi circular arc, placing the test lens or gauge in front of the aperture 28. A two fingered metal spring 20 is attached to one of the support brackets and presses against the smaller disc 13, to prevent its rotation in the support brackets.

On the extended tip portion of the front surface of the clamping member 21 are lateral rulings 37 which are used for correlating distances of the bottom of a test lens or the pupil location gauge relative to the bottom of a spectacle socket. The top half of the aperture 28 carries angular rulings 38 which are used to indicate angular orientation of a test lens, for measuring the angular alignment of a test lens, as in astigmatism correction.

Figure 2:
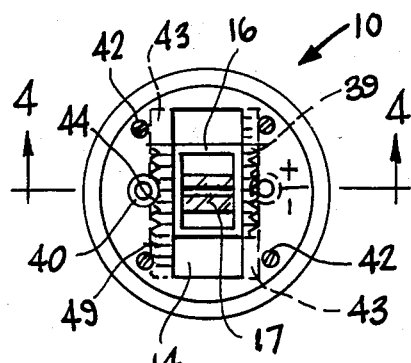
FIGS. 2 and 3 are front and rear views of the pupil location gauge.
Figure 3:
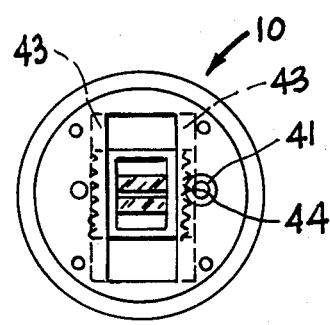

A front view of a preferred embodiment of the pupil location gauge is shown in FIG. 2. The frame insert 16 holding the filter 17 extends into slots 43 between the two discs. Screws 42 hold the discs together retaining the insert in the slots also shown in cross section in FIG. 4. A pinion gear hole 40 approximately 5 mm diameter is shown in FIG. 2. Some of the teeth 44 of the rack member 39 on the edge of the insert show in the hole. Insertion of a pinion gear 45 (not shown) into the gear hole engaging the teeth of the rack drives the insert bearing the filter up and down in the slots. Gear holes 40 and 41 are set in front and back respectively and a rack is located on both sides of the insert providing means of moving the insert from either front or back. Calibrated rulings 49 are shown on both edges of the disc bordering the aperture 14. On one edge the rulings are calibrated from the bottom edge of the disc. On the other edge the rulings are calibrated from the mid section of the disc. The rear view shown in FIG. 3 shows the gear hole 41 and teeth of the rack on the other edge of the insert.

Figure 4:
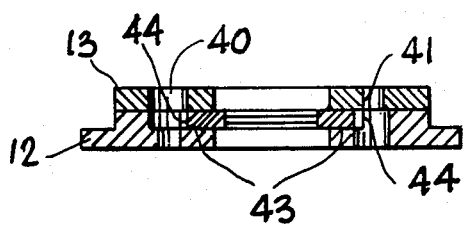
FIG. 4 is a cross section of the pupil location gauge taken along lines 4—4 of FIG. 2.

FIG. 4 shows the cross section of the gauge taken along lines 4—4 of FIG. 2. The insert 16 carrying the filter 17 is held between the two discs 12 and 13 in the slots 43. The teeth 44 of the rack are seen extending into the gear holes 40 and 41.

Figure 5:
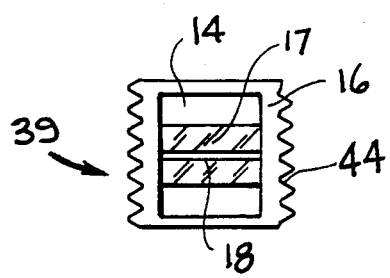
FIG. 5 is a front view of an index member.
Figure 6:
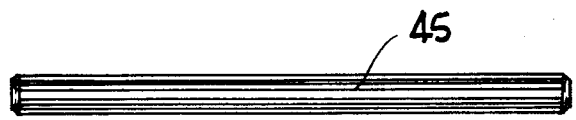
FIG. 6 is a side view of a pinion gear.
Figure 7:
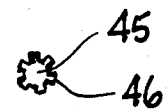
FIG. 7 is an end view of a pinion gear.

FIG. 5 shows the teeth edges 44 on the insert 16 comprising the rack member 39 of the moving means of the pupil location gauge. A pinion gear member 45, approximately 30–40 mm long and 5 mm in diameter, shown in FIG. 6 and FIG. 7 is inserted at either 41 or 40 to engage the teeth 44 of the rack 39 with the teeth 46 of the gear member thereby moving the insert in relation to the calibrated rulings 49 of the aperture 15 shown in FIG. 1 and FIG. 2.

Other means of moving the vision interference index member may be used. For example, an end of a finely threaded screw may be attached to the bottom edge of the frame holding the index member. The thread of the screw would engage a threaded bore formed in a side wall of the disc and exit in a base portion having a surface suitable for rotation of the screw between thumb and forefinger.

The gauge and lens holder may be used for either monocular or binocular measurement of the pupil location in the following manner. The gauge may be placed in the aperture of the holder by inserting the smaller diameter disk in the back side of the front clamping member for measurement with empty spectacle frames where the gauge would lie in the plane of the lens socket. The gauge may also alternately be held by the brackets on the front of the holder along with test lens. The holder is then clipped over a lens socket of a spectacle frame so that the bubble in the level in the handle is centered on the index of the handle. For measurement of the pupil location for correct placement of a corrective power vertically in a progressive lens the gauge is aligned in the holder so that the center line 18 of the filter insert is horizontal with the rulings calibrated from the base located at the left. While the patient views either a close or distant object the filter insert is moved vertically by means of the rack and pinion gear to a point at which the object is blocked out by the red filter. The measurement indicated by position of the center line against the calibrated scale added to the lateral ruling distance from the bottom edge of the socket to the bottom edge of the gauge gives the proper pupil vertical location for near or distance viewing.

Two lens holders may be joined for binocular measurement by means of the slotted handle member 32 as shown in FIG. 9. A scaled rod 46 is slid through the slots of the handles of two lens holders so that the rulings 47 are visible through the window 35. The two lens holders are clipped to the two lens sockets of a spectacle frame 48 as shown. The pupil location gauge is then moved as discussed above to measure the vertical pupil location of each eye. The gauge is then rotated 90° so that the center line 18 of the filter insert is in a vertical position and the rulings calibrated from the midsection located at the top as shown in FIG. 9. The filter is then moved horizontally until the view by one open eye of a distant or far object is blocked by the filter. The test is repeated with the other eye. The distance on the scaled rod 46 between the index lines 34 of the handle of the two lens holder plus or minus the correction measured by each of the pupil location gauges is the horizontal interpupillary distance, the distance between the line of sight of one eye and the line of sight of the other eye at a point in a near or far plane. This distance may also be measured monocularly with one lens holder by centering the scaled rod over the center of the spectacle nose piece and measuring the pupillary distance from that point for each eye using one lens holder.

The parts of the gauge may be machined or molded and may be of metal or plastic. In the preferred embodiment, the filter is preferably red but other filters which lower visible light transmission may be used. The vision interference index member does not have to be a filter but can be any material which partially lessens the field of vision so that the index is superimposed on a near or distant object.

The mechanical means for moving the index member may be of a rack and pinion gear as in the preferred embodiment or alternately a thumb screw attached to one end of the index member through the disc side wall.

The pupil location gauge used with an ophthalmic lens holder of the type shown yields an accurate measurement of the vertical and horizontal pupillary distance with respect to a spectacle frame due to the correlation between rulings on the gauge and the lens holder obtainable with the lens holder of U.S. Pat. No. 4,381,143. However, the pupil location gauge of the present invention may be used with any type of ophthalmic test lens holder having a means of correlating the placement of the gauge with dimensions of the spectacle frame.

I claim:

1. A pupil location gauge for use in an ophthalmic test lens holder comprising, a disc mountable in a test lens holder having a graduated scale and an insert containing a vision interference index member, said index member comprising a material which decreases visual light transmission, having a center line intersecting the visual axis, and mechanical means associated with said disc for moving said insert to change the position of said index member in relation to the graduated scale on said disc.

2. The gauge of claim 1 wherein said material is a filter.

3. The gauge of claim 1 wherein said means for moving said insert comprises a rack and pinion gear.

4. The gauge of claim 1 wherein said means for moving said insert comprises a screw in the side wall of said disc.

5. A pupil location gauge for use in an ophthalmic test lens holder comprising, a disc having a central aperture seating a movable insert, said insert having rack edges mating with a pinion gear, said insert having an optical filter member, having a center line intersecting the visual axis, said disc bearing lateral rulings near the aperture forming a graduated scale at an edge proximate to said filter whereby relative position of the filter is indexed on said scale.

6. A pupil location gauge for use in an ophthalmic test lens holder comprising, a disc mountable in a test lens holder having a central aperture with a movable insert therein bearing a narrow filter, and having a center line intersecting the visual axis, said insert movable by means of a pinion gear cooperating with a rack affixed to the insert, said disc having lateral rulings near the aperture forming a graduated scale whereby the position of said filter is indexed relative to a base of said disc.

7. A pupil location apparatus for use with spectacle frames comprising,
   (a) a pupil location gauge comprising a disc having a central aperture with a movable insert therein bearing a vision interference index member, said index member comprising a material which decreases visual light transmission, having a center line intersecting the visual axis, and having mechanical means associated with said disc for movement of said insert in said aperture, said disc having lateral rulings forming a graduated scale adjacent said aperture whereby a position of said index member is changed relative to a base of said disc,
   (b) an ophthalmic test lens holder having said pupil location gauge mounted therein, said holder comprising,
      (i) an elongated first clamping member defining a first aperture therein,
      (ii) an elongated second clamping member, defining a second aperture therein, said second clamping member facing said first clamping member and spaced therefrom a distance accommodating a spectacle frame therebetween, with said first and second clamping members being elongated and having an extended tip with a clamping member length substantially greater than a lens socket in the spectacle frame intended to be placed between said clamping members such that the clamping members may adjustably be disposed across and contact opposed sides of a lens socket of said spectacle frame, spanning the dimension of the socket, the first of said clamping members having a plurality of parallel lateral rulings thereon, for referencing an aperture relative to the socket, the number and extent of lateral rulings being sufficient to reference the position of a test lens held over an aperture with respect to said socket,
      (iii) spring means connected to said first and second clamping members for resiliently biasing said first clamping member toward said second clamping member, and
      (iv) bracket means attached to one of said clamping members for removably holding said pupil location gauge over said first aperture.

8. The pupil location apparatus of claim 7 wherein said material is a filter having a light obscuring mark thereon.

9. The pupil location apparatus of claim 7 wherein said means for movement of said insert comprises a pinion gear mounted in said disc and a rack affixed to said movable insert.

10. The pupil location apparatus of claim 7 wherein said lens holder has a slotted handle at the top of the first clamping member, said handle having indicia for referencing the position of said lens holder relative to a graduated scale on a bar extending through said slot for the measurement of horizontal interpupillary distance.

11. The pupil location apparatus of claim 10 wherein said lens holder is slidably fastened in relation to another lens holder by means of the bar extending through said slotted member.

* * * * *